United States Patent [19]

Mahone

[11] 4,222,953
[45] Sep. 16, 1980

[54] METHOD OF PREPARING ORGANOSILOXANES AND METHYLCHLORIDE

[75] Inventor: Louis G. Mahone, Midland, Mich.

[73] Assignee: Dow Corning Corporation, Midland, Mich.

[21] Appl. No.: 64,153

[22] Filed: Aug. 6, 1979

[51] Int. Cl.² .............................................. C07F 7/08
[52] U.S. Cl. ................................................... 260/466
[58] Field of Search ................................. 260/448.2 E

[56] References Cited

U.S. PATENT DOCUMENTS

| 2,556,897 | 6/1951 | Bidaud | 260/448.2 E |
| 2,741,630 | 4/1956 | Reed et al. | 260/448.2 E |
| 3,432,538 | 3/1969 | Curry | 260/448.2 E |
| 3,484,468 | 12/1969 | Curry | 260/448.2 E |
| 3,576,023 | 4/1971 | Curry | 260/448.2 E |
| 3,803,195 | 4/1974 | Nitzsche et al. | 260/448.2 E |
| 4,108,882 | 8/1978 | Mahone | 260/448.2 E |

FOREIGN PATENT DOCUMENTS 1538609  1/1979  United Kingdom ............. 260/448.2 E Primary Examiner—Paul F. Shaver
Attorney, Agent, or Firm—James E. Bittell

[57] ABSTRACT

Organochlorosilanes are reacted with methanol in contact with a tetraorganophosphonium chloride catalyst to form organosiloxanes and methylchloride. The method avoids significant silicon-carbon bond cleavage and provides good conversion of the chlorine of the chlorosilane to methylchloride while avoiding undesirable dimethylether formation.

12 Claims, No Drawings

METHOD OF PREPARING ORGANOSILOXANES AND METHYLCHLORIDE

BACKGROUND OF THE INVENTION

This invention relates to the reaction of organochlorosilanes with methanol in the presence of a tetraorganophosphonium chloride catalyst to produce organosiloxanes, methylchloride and water.

At present the primary commercial method for preparing methylsiloxanes is by hydrolysis of methylchlorosilanes to give methylsiloxanes and hydrogen chloride. Recovered hydrogen chloride is reacted with methanol to produce methylchloride which in turn is reacted with silicon metal to form the methylchlorosilanes. The chlorine cycle constitutes three steps: (1) hydrolysis to give hydrogen chloride, (2) reaction of hydrogen chloride with methanol to give methylchloride, and (3) reaction of methylchloride with silicon metal. It is highly desirable to reduce this to a two step cycle by combining steps (1) and (2) so that chlorosilane is reacted with methanol to give siloxane and methylchloride according to the equation $$Me_nSiCl_{4-n} + (4-n)MeOH \rightarrow (4-n)MeCl + (4-n)/2 H_2O + Me_nSiO_{(4-n)/2}$$

where n can be 2 or 3 and Me represents the methyl radical.

Reactions of chlorosilanes with methanol to give organosiloxanes and methylchloride according to the above equation are not new. U.S. Pat. No. 2,556,897 discloses a liquid phase reaction of dimethyldichlorosilane with methanol. No catalyst is suggested. A viscous siloxane product was obtained. U.S. Pat. No. 2,741,630 describes the same reacion at a temperature of 175° C. in the presence of ZnCl$_2$ on silica gel. U.S. Pat. No. 3,803,195 shows the reaction of methanol with Me$_n$SiCl$_{4-n}$ by a countercurrent flow method in which the column is packed with an essentially inert and acid resistant packing material. The patent teaches col. 4, lines 6-12, that catalytic agents such as Lewis acids and cation exchange resins in the H-form may be used with the packing materials, but the use of such materials is not desirable and should be avoided since these materials tend to promote the cleavage of silicon-carbon bonds.

U.S. Pat. No. 4,108,882 by the same inventor as the instant application describes the vapor phase reaction of methanol and methylchlorosilanes in the presence of quaternary ammonium chloride salt catalyst. The method results in improved yields of methylsiloxanes and methylchloride without significant cleavage of silicon-carbon bonds. In addition, the method gave only low yields of dimethylether as a contaminant in the methylchloride.

SUMMARY OF THE INVENTION

It has been discovered that excellent yields of organosiloxanes of the formula R$_n$SiO$_{(4-n)/2}$ where R is an alkyl radical of 1 to 4 carbon atoms and n has an average value from 1.95 to 3 can be obtained without significant silicon-carbon bond cleavage by heating a mixture of the corresponding organochlorosilane and methanol in the presence of a tetraorganophosphonium chloride salt catalyst. The catalyst provides an accelerated reaction rate and gives good conversion of the chlorine from the chlorosilane to methylchloride while the co-production of dimethylether is low. Useful catalysts are of the general formula R'$_4$PCl wherein R' is independently selected from the group consisting of alkyl radicals of 1 to 10 carbon atoms and aryl radicals of 6 to 10 carbon atoms.

DETAILED DESCRIPTION OF THE INVENTION

The tetraorganophosphonium chloride salts employed as catalysts in the method of this invention are well known compounds obtained by reacting triorganophosphines with alkyl and aryl chlorides. Among the types of radicals that can be included as the R' substituent on the phosphonium chloride are alkyl radicals such as methyl, ethyl, butyl, and octyl and aryl radicals such as phenyl, tolyl, naphthyl and propylphenyl. Catalysts that can be used in the method of the present invention include tetrabutylphosphonium chloride, tripentylmethylphosphonium chloride, tetrapropylphosphonium chloride, tetraphenylphosphonium chloride, tetratolylphosphonium chloride, and triphenylmethylphosphonium chloride.

The catalyst is normally present as the quaternary phosphonium chloride salt, but any halide salt capable of conversion to the chloride form in situ may be employed. For example, the corresponding bromide or iodide salts can be used since they will soon be converted to the chloride salt during the reaction.

The catalyst can be employed in a solid or molten form. If the solid form is selected, the catalyst is best absorbed upon a suitable carrier or support means. The specific carrier or support means employed is not critical. Any known type can be used such as charcoal, diatomaceous earth or silica gel, etc. Again, it is not critical what method is used to absorb the catalyst onto the support. One such acceptable method, however, comprises dissolution of the catalyst in an appropriate solvent such as methylene chloride in such amounts that when the catalyst-solvent solution is mixed with the support, and the mixture of ingredients dried to remove substantially all of the solvent, there remains deposited on the support, in a homogeneous fashion, the recited amount of catalyst.

The amount of catalyst by weight in combination with the support may range widely. The upper range is limited to such quantities as would enhance the free accessibility of the catalyst to the vapors with which it must come in contact. Also economic considerations and the physical dimensions of the reactor play a key role in determining the amount of catalyst employed.

Of course, the presence of the catalyst in too low an amount may result in lower alkyl chloride conversion than is optimally obtainable with higher amounts of catalyst present. However, determining the "proper" catalytic amounts needed depends upon a variety of factors and is best determined empirically.

The organochlorosilanes that can be convereted to siloxanes without significant silicon-carbon bond cleavage by the method of this invention are triorganochlorosilanes and diorganodichlorosilanes of the formula R$_n$SiCl$_{4-n}$ where R is an alkyl radical of 1 to 4 carbon atoms and n has an average value of 1.95 to 3. Monochlorosilanes that can be reacted include trimethylchlorosilane, triethylchlorosilane, and tributylchlorosilane. Dichlorosilanes that can be reacted include dimethyldichlorosilane, propylmethyldichlorosilane, diethyldichlorosilane, and butylmethyldichlorosilane, etc. Mixtures of the monochlorosilanes and dichlorosilanes can also be reacted.

When the silane is a triorganochlorosilane the primary siloxane product is hexaorganodisiloxane. In addition there can be trace amounts of octaorganotrisiloxane produced due to methyl cleavage. When the silane reactant is a diorganodichlorosilane such as dimethyldichlorosilane the primary siloxane products are cyclodiorganosiloxanes.

In carrying out the method of this invention, it is preferred to react the methanol and the silane while both reactants are in the vapor phase. Any standard method of vaporization can be utilized as, for example, vaporization through glass beads. The vapor phase reaction is preferred because it provides the best yield of the volatile cyclodiorganosiloxanes which are useful in preparing many silicone products.

In a preferred embodiment of the invention, the molten catalyst or the solid form in combination with the support, are packed into a suitable reactor device which is preceded by a volatilizing zone. Although it is not necessary, the volatilizing zone can contain finely divided material such as glass beads to aid in volatilizing the reactants. The reactants are individually introduced into the volatilizing zone and the vapors formed are mixed and passed through the catalyst zone. Thereafter, the volatile reaction products as well as any unreacted materials can be led into suitable condensing traps maintained at various temperatures designed to effect condensation of the reaction products.

The reaction can be carried out advantageously when the temperature of the catalyst zone is maintained within the range of about 90° C. to 230° C. If temperatures below about 90° C. are used the rate of the reaction may be undesirably slow. The optimal temperature range is believed to be about 120° to 200° C. based upon present economical considerations. Of course, the upper temperature limit should be below the temperature at which significant decomposition of the catalyst could occur. One of the advantages of the catalysts of this invention is their good thermal stability.

The preferred pressure of this reaction is maintained at atmospheric although it may be carried out under conditions below, at, or above atmospheric. One skilled in the art will recognize that the pressure temperature relationship should be such that water escapes from the reaction zone. Otherwise the water formed during the reaction could accumulate to a point where the catalyst would be rendered ineffective.

The proportions of initial reactants used are not critical. It is obvious to one having ordinary skill in the art, however, that a reasonable excess of alcohol is beneficial where it is desired to convert substantially all of the chlorine from the chlorosilane to methylchloride. Ratios of one to one or a slight excess of silane might also be employed. For efficient operation, the ratio of reactants preferably ranges from about 10 mole percent excess of chlorosilane to about 30 mole percent excess of methanol.

In order that those skilled in the art may better understand how the present invention may be practiced, the following examples are given as an illustration and are not intended to serve as a limitation.

EXAMPLE 1

A column with a 9 mm inside diameter was packed with a 50 ml volume of charcoal impregnated with 2 g of tetrabutylphosphonium chloride. The column was maintained at a temperature of 160° C. with a hot air oven. Trimethylchlorosilane and methanol were injected into the column at one end with variable speed syringe pumps. Upon entering the column, the silane and methanol were vaporized while passing over a short section of glass beads prior to the charcoal. The feed rates were adjusted to give 15 mole percent excess methanol with a total gas hourly space velocity (GHSV) flow of 150 hr$^{-1}$. After an initial 10 to 20 minutes of operation, the effluent from the column was passed through a cold trap to collect the siloxane products. Product was collected over a 20 minute period and analyzed. Greater than 99 percent conversion to hexamethyldisiloxane was observed with only 0.005 m mole of octamethyltrisiloxane detected per gram of siloxane product. This corresponds to methyl cleavage of 0.04 percent of the silane feed. The conversion to methylchloride was 90.6 percent with remaining chlorine from the chlorosilane collected as aqueous HCl. The methylchloride collected also contained 0.10 mole percent dimethylether.

EXAMPLE 2

The experiment in Example 1 was repeated employing 4 g of catalyst per 50 ml of charcoal. The column was maintained at 190° C. and the GHSV flow was 300 hr$^{-1}$. Again greater than 99 percent conversion of the trimethylchlorosilane to hexamethyldisiloxane was obtained. Octamethyltrisiloxane was detected corresponding to methyl cleavage of 0.08 percent of the silane feed. The conversion to methylchloride was 91 percent with remaining chlorine from the chlorosilane collected as aqueous HCl. The methylchloride collected contained only 0.05 mole percent dimethylether.

EXAMPLE 3

A column with a 9 mm inside diameter was packed with 60 ml volume of 12–20 mesh charcoal impregnated with 6.5 g of tetraphenylphosphonium chloride. Trimethylchlorosilane and methanol were injected into one end of the column as in Example 1 to give a GHSV flow of 150 hr$^{-1}$ except that 20 percent excess methanol was employed. The column temperature was varied as shown in Table 1. The conversion of silane to siloxane was essentially quantitative. The conversion of chlorine from the chlorosilane to methylchloride and the mole percent of dimethylether in the methylchloride at various column temperatures are shown in Table 1.

Table 1

| Temperature | Percent Conversion to MeCl | Mole Percent Me$_2$O in the MeCl |
| --- | --- | --- |
| 120 | 74 | 0.4 |
| 135 | 82 | 0.2 |
| 150 | 99.54 | — |
| 165 | 99.92 | 0.5 |

EXAMPLE 4

This example illustrates the use of a molten phosphonium chloride salt as catalyst in the method of this invention.

Dimethyldichlorosilane at a rate of 12.47 ml per hour and methanol at a rate of 9.23 ml per hour were vaporized and passed through a dip tube into a 26.0 ml reservoir of molten tetrabutylphosphonium chloride. The reservoir was maintained at 185° C. and atmospheric pressure. The flow rates correspond to a 19 percent excess of methanol and a liquid hourly space velocity of 0.83 hr$^{-1}$.

The experiment was continued for 7.5 hours so that reactants equivalent to 6.2 times the reactor volume were passed through the catalyst zone. No loss in catalyst volume or activity was noted. Also no accumulation of siloxane products was noted in catalyst zone of the reactor.

The conversion of chlorine from the chlorosilane to methylchloride was 92 percent with remaining chlorine collected as aqueous HCl. The methylchloride collected also contained 0.34 mole percent dimethylether.

The conversion of silane to siloxanes was essentially quantitative. The siloxane product was found by gas-liquid phase chromatography to contain 75.7 percent by weight dimethylsiloxane cyclics. Phosphorous at 200 ppm was also detected in the siloxane product.

That which is claimed is:

1. A method for reacting a chlorosilane of the formula (1) $R_nSiCl_{4-n}$ with (2) methanol to produce siloxanes of the formula $R_nSiO_{4-n/2}$ and methylchloride in which R is an alkyl radical of 1 to 4 carbon atoms and n has an average value from 1.95 to 3, consisting essentially of heating a mixture of (1) and (2) in contact with a tetraorganophosphonium chloride salt catalyst of the formula $R'_4PCl$ wherein each R' is independently selected from the group consisting of alkyl radicals of 1 to 10 carbon atoms and aryl radicals of 6 to 10 carbon atoms.

2. The method of claim 1 wherein the chlorosilane and methanol are in the vapor phase when contacted with the catalyst.

3. The method of claim 1 wherein the tetraorganophosphonium chloride is formed by conversion of a corresponding tetraorganophosphonium bromide or iodide to the chloride during the reaction.

4. The method of claim 2 wherein the chlorosilane and methanol vapors are contacted with the catalyst at 90° C. to 230° C.

5. The method of claim 2 wherein the chlorosilane and methanol vapors are contacted with the catalyst at 120° C. to 200° C.

6. The method of claim 2 wherein the ratio of reactants ranges from about 10 mole percent excess of chlorosilane to 30 mole percent excess of methanol.

7. The method of claim 6 wherein the chlorosilane is dimethyldichlorosilane.

8. The method of claim 6 wherein the chlorosilane is trimethylchlorosilane.

9. The method of claim 6 wherein the catalyst is tetrabutylphosphonium chloride.

10. The method of claim 6 wherein the catalyst is tetraphenylphosphonium chloride.

11. The method of claim 6 wherein the catalyst is employed in the molten state.

12. The method of claim 6 wherein the catalyst is employed in a solid form absorbed on a suitable support means.

* * * * *